(12) United States Patent
Bordoloi et al.

(10) Patent No.: US 6,998,411 B2
(45) Date of Patent: Feb. 14, 2006

(54) 2-METHYLHEPTYLISONICOTINATE AND PROCESS FOR PRODUCTION THEREOF

(75) Inventors: Gojendra Nath Bordoloi, Assam (IN); Babita Kumari, Assam (IN); Nabibjyoti Bordoloi, Assam (IN); Monoj Kanti Roy, Assam (IN); Tarun Chandra Bora, Assam (IN)

(73) Assignee: Council of Scientific and Industrial Research, New Delhi (IN)

( * ) Notice: Subject to any disclaimer, the term of this patent is extended or adjusted under 35 U.S.C. 154(b) by 182 days.

(21) Appl. No.: 10/027,913

(22) Filed: Dec. 20, 2001

(65) Prior Publication Data

US 2002/0161027 A1 Oct. 31, 2002

(51) Int. Cl.
*A01N 43/40* (2006.01)

(52) U.S. Cl. .................. 514/354; 514/356; 546/314; 546/315; 435/117

(58) Field of Classification Search .............. 514/354, 514/356; 546/314, 315; 435/117
See application file for complete search history.

(56) References Cited

PUBLICATIONS

Bordoloi et al., Bioscience, Biotechnology, and Biochemistry (2001), 65(8), 1856–1858.*

* cited by examiner

*Primary Examiner*—Irene Marx
(74) *Attorney, Agent, or Firm*—Darby & Darby

(57) ABSTRACT

The present invention relates to a novel antifungal antibacterial compound 2-methylheptylisonicotinate of formula 1 below obtained from natural sources and to a process for the isolation thereof.

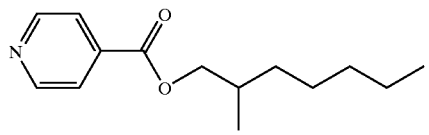

1

2 Claims, No Drawings

2-METHYLHEPTYLISONICOTINATE AND PROCESS FOR PRODUCTION THEREOF

The present invention relates to a novel antifungal and antibacterial compound 2-methylheptylisonicotinate of formula 1 isolated from natural sources. The present invention also relates to a process for the production of 2-methylheptylisonicotinate of formula 1.

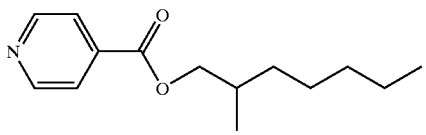

This invention also relates to a process for the production of an anti-fungal and antibacterial antibiotic produced by *Streptomyces* sp. 201 which exhibited marked inhibition of bacterial strains such as, *Bacillus subtilis, Shigella* sp., *Klebsiella* sp., *E. coli*. and *Proteus mirabilis* and antifungal activity against pathogenic test organisms, such as *Fusarium moniliforme, F. semitechtum, F. oxysporum, F. solani* and *Rhizoctonia solani*. The organism *Streptomyces* sp. 201 has the MTCC designation number 5105, having been deposited on Jul. 16, 2003 (Microbial Type Culture Collection & Gene Bank, India). In another aspect the invention relates to a method for the treatment of tuberculosis using compound of formula 1 or a pharmaceutically acceptable derivative thereof.

BACKGROUND OF THE INVENTION

Research is constantly on to obtain antifungal and antibacterial compounds from natural sources such as microorganisms. Several naturally occurring microorganisms form an excellent source of pharmaceutically acceptable compounds which have the advantage of being inexpensive since the expense of technology to manufacture synthetic compounds is avoided.

2-methylheptylisonicotinate is an important anti-fungal and antibacterial antibiotic which exhibits marked inhibition of bacterial strains such as, *Bacillus subtilis, Shigella* sp., *Klebsiella* sp., *E. coli* and *Proteus mirabilis* and antifungal activity against pathogenic test organisms, such as *Fusarium moniliforme, F. semitechtum, F. oxysporum, F. solani* and *Rhizoctonia solani*.

2-methylheptylisonicotinate of the formula 1 is also used as an intermediate for the highly economical commercial production of isoniazid or isonicotinic acid hydrazide. Isoniazid or isonicotinic acid hydrazide of the formula 2 is an established drug for the treatment of Tuberculosis (Martindale: The Extra-pharmacopeia, ed. J. E. F. Reynolds, 30th edition, The Pharmaceutical Press, London, U.K., 1993, pp174).

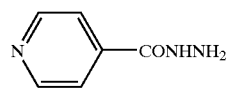

Nearly 500,000 patients die of Tuberculosis in India every year and 5.3 million new cases of Tuberculosis are reported every year in the world (Kalia A, 1999, A Deadly Bacilli, A report, 1999, The Statesman, Calcutta, 7th Apr., pp7).

It is therefore imperative to locate and identify new sources for anti-tubercular drugs.

OBJECTS OF THE INVENTION

The main object of the present invention is to provide a process for the preparation of 2-methylheptylisonicotinate from culture filtrate of a bacteria isolated from soil.

Another object of the present invention is to provide a process for the isolation of a bacteria from soil christened as *Streptomyces* species 201 culture filtrate of which can be used to produce -2-methylheptylisonicotinate of the formula 1.

Another object of the present invention is to provide a process for the isolation of a bacteria from soil christened as *Streptomyces* species 201 culture filtrate which is commercially feasible and economical.

Yet another object of the present invention is to provide a process for the production of 2-methylheptylisonicotinate useful as an intermediate for the economical commercial production of isoniazid or isonicotinic acid hydrazide.

Still yet another object of the present invention is to provide an improved process for the production of isoniazid or isonicotinic acid 2-methylheptyl ester from the culture broth of the *Streptomyces* species 201 by use of a simple culture medium without using any intermediate additives

SUMMARY OF THE INVENTION

Accordingly, the present invention relates to a novel antifungal antibacterial compound 2-methylheptylisonicotinate of formula 1 below obtained from natural sources.

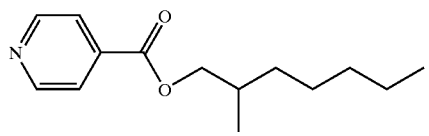

In one embodiment of the invention, the compound of formula 1 is obtained from *Streptomyces* sp. 201.

The present invention also relates to a process for the isolation of a novel antifungal antibiotic compound 2-methylheptylisonicotinate of formula 1 below

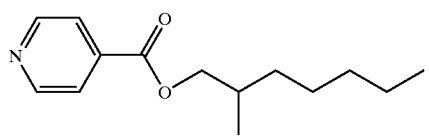

said process comprising growing *Streptomyces* species 201 in a nutrient medium and isolating the compound of formula 1 therefrom.

In an embodiment of the invention, nutrient medium comprises Thronton's medium.

In a further embodiment of the invention, Thronton's medium comprises the following ingredients in g/L: Dipotassium hydrogen phosphate ($K_2HPO_4$) 0.8 to 1.5, potassium nitrate ($KNO_3$) 0.3 to 1.0, magnesium sulfate ($MgSO_4$) 0.1 to 0.4, calcium chloride ($CaCl_2.2H_2O$) 0.0.5 to 0.2, asparagine 0.2 to 0.7, mannitol 0.1 to 2.0, sodium chloride (NaCl) 0.05 to 0.3, ferric chloride ($FeCl_3$) 0.01 to 0.05 at pH in the range of 6.5 to 9.0.

In a preferred embodiment of the invention, the Thronton's medium comprises of the following ingredients in g/L: $K_2HPO_4$ 1, $KNO_3$ 0.5, $MgSO_4$ 0.2, $CaCl_2.2H_2O$ 0.1, asparagine 0.5, mannitol 0.1, NaCl 0.1, $FeCl_3$ 0.01 at pH of 7.4.

In another embodiment of the invention, *Streptomyces* sp. 201 is grown on nutrient agar at pH 7 to 9 for a period of 6 days followed by inoculating in Thronton's medium at a pH in the range of 7 to 9 for at least 3 days, the culture broth being then extracted with a water immiscible solvent, followed by evaporating the solvent to get a crude oily substance, and purifying the 2-methylheptylisonicotinate from the crude oil.

In another embodiment of the invention, nutrient agar has the following ingredients in g/L: beef extract 2.5 to 6.0, peptone 3.5 to 7.0, potassium nitrate 0.8 to 1.4, agar 14 to 23.

In yet another embodiment of the invention, growing and inoculation are effected at a temperature in the range of 28 to 32° C.

In still another embodiment of the invention, extraction of broth is effected by a water immiscible solvent selected from the group consisting of hydrocarbons such as hexane, heptane, petroleum ether, benzene and toluene, halogenated solvents selected from chloroform, dichloromethane and ethylene dichloride and lower acid esters such asmethyl acetate, ethyl acetate and propyl acetate.

In a further embodiment of the invention, the purification is done by by chromatographic methods.

In another embodiment of the invention, yield of compound of formula 1 2-methylheptylisonicotinate is 2.5 mg from 500 ml of cell free culture filtrate.

The invention also relates to a method of treatment of tuberculosis comprising administering to a animal a pharmaceutically acceptable dose of compound of formula 1 or a pharmaceutically acceptable derivative thereof.

DETAILED DESCRIPTION OF THE INVENTION

The process of the present invention does not involve the use of any high boiling solvent and also does not involve the use of costly and environmentally toxic catalysts. The recovery of the solvent is also possible which makes the process simple and economic. The process of the present invention has been developed using a very non-toxic, easily isolable micro-organism identified as *Streptomyces* species 201.

The process of the invention for producing this new highly active antibacterial and antifungal compound prepared according to the process of the present invention is very simple and economical. Therefore, the simplicity of the economical and environmentally acceptable nature of the process developed by this invention makes the process commercially viable and important.

The process for production of 2-methylheptylisonicotinate of the formula 1 generally comprises growing *Streptomyces* sp. 201 on nutrient agar at pH 7 to 9 for a period of 6 days by inoculation in Thronton's medium at pH in the range of 7 to 9 for at least 3 days, extracting culture broth with water immiscible solvent, evaporating solvent to get crude oily substance, purifying 2-methylheptylisonicotinate from crude oil by chromatographic methods.

Nutrient agar has following ingredients in g/L: beef extract 2.5 to 6.0, peptone 3.5 to 7.0, potassium nitrate 0.8 to 1.4, agar 14 to 23. The inoculation may be effected in Thronton's medium having following ingredients in g/L: Dipotassium hydrogen phosphate ($K_2HPO_4$) 0.8 to 1.5, potassium nitrate ($KNO_3$) 0.3 to 1.0, magnesium sulfate ($MgSO_4$) 0.1 to 0.4, calcium chloride ($CaCl_2.2H_2O$) 0.0.5 to 0.2, asparagine 0.2 to 0.7, mannitol 0.1 to 2.0, sodium chloride (NaCl) 0.05 to 0.3, ferric chloride ($FeCl_3$) 0.01 to 0.05 at pH in the range of 6.5 to 9.0. Preferably growing and inoculation is effected at a temperature in the range of 28 to 32° C.

Extraction of the broth is effected by water immiscible solvents selected from a group consisting of hydrocarbons such as hexane, heptane, petroleum ether, benzene, toluene, halogenated solvents and lower acid esters such as methyl acetate, ethyl acetate, propyl acetate. The present invention provides a process for the production of 2-methylheptylisonicotinate of the formula 1 and its bio-evaluation which comprises:

a) Isolation of the Micro-organism:

A loopful of spores from slant cultures of *Streptomyces* sp. 201, grown on nutrient agar was inoculated in Thronton's medium, at 30° C. in a gyratory shaker, 3.3 Hz, at 200 r.p.m. for 6 days. Both live broth and purified compound from the live broth showed very good antibacterial and antifungal activities against a number of pathogenic organisms. The strain was collected from tea garden soils in Jorhat, Assam (26°44'N and 94°10'E). The morphological and physiological observation of *Streptomyces* sp. 201, on nutrient agar exhibited flexible hyphae from branched aerial mycelium. Most of the mature spore chains comprised of 30 or more spores (0.7~1.0×1.0~1.32 $\mu$m) with smooth surface. No sporongia or synnemata were observed. The vegetative mycelia were not fragmented into Bacillary and coccoid forms and the conidia were borne as sporophores indicating that the organisms belongs to the family *Streptomycetaceae* and to the genus *Streptomyces*, as evident by the production of chains of conidia in aerial hyphae.

b) Biological Activity of the Live Broth:

Live broth of cultured organism *Streptomyces* sp. 201 showed very good antibacterial and antifungal activities against a number of pathogenic organisms. To assess the antifungal activity of the live broth, agar cup assay method was followed. 200 $\mu$l of the live broth was added into each agar cup. Zone of inhibition was found more *R. solani* (13 mm), followed by *F. oxysponim* and *F. moniliformae* (12 mm) *F. solani* (11 mm) and *F. semitechtum* (10 mm). The same procedure was observed more in *E. coli* (12 mm) followed by *P. mirahilis* and *Klebsiella* sp. (12 mm), *Shigella* sp. (9 mm) and *B. subtilis* (8mm). (Table 1 below)

TABLE 1

| Biological activity of the live broth Strains Inhibition zone (mm) at 200 $\mu$g | | | |
|---|---|---|---|
| Antifungal activity | | Antibacterial activity | |
| *Fusarium moniliforme* | 12 | *Bacillus subtilis* | 8 |
| *F. semitechium* | 10 | *Shigella* sp. | 9 |
| *F. oxysporum* | 12 | *Klebsiella* sp. | 11 |
| *F. solani* | 11 | *E. coli* | 12 |
| *Rhizoctonia solani* | 13 | *Proteus mirahilis* | 11 | c) Isolation of the Anti-fungal, Antibacterial Compound:

The bio-active compound was isolated as an oil by removing the cell mass through centrifugation followed by extraction (ethyl acetate) and purification by TLC. However, the cell mass can also be extracted with chloroform, dichloromethane, ethylene dichloride and other halogenated solvents, hexane, heptane, petroleum ether (40–60° C. fraction, 60–80° C. fraction or 80–100° C. fraction), and other petroleum derived solvents, methyl acetate, propyl acetate, benzene, toluene or any organic solvent. The purification can be affected with column chromatography, medium pressure liquid chromatography (MPLC), high pressure liquid chromatography (HPLC) or other chromatographic methods. Purification can also be affected with fractional distillation, short path distillation etc. The compound was analyzed for $C_{14}H_{21}NO_2$ by elemental analysis and EIMS giving molecular ion at 235. The mass spectrum further gave ions at m/z 149, 126, 122, 106, 113, 99, 78 and 58. The UV spectrum of it showed $\lambda_{max}$ at 220 nm. The IR spectrum of it showed absorption band at 2935, 2900, 2850, 2335, 2320, 1715, 1560 cm$^{-1}$ indicating the presence of aromatic system with C=N— and ester group. In the $^1$H NMR spectrum, two doublets of doublet with J=4 and 6 Hz, each integrating to two protons at δ 7.5 and 7.7 indicates the presence of the pyridyl system in the molecule The multiplet signal at δ 4.22 integrating to one proton confirms the presence of the ester group. The doublet at δ 0.93 with J=7Hz and a triplet at δ 0.88 with J=7Hz, each integrating to three protons indicate the presence of two methyl groups. The DEPT experiment of the compound indicated the presence of four aromatic CH, two methyl groups, five methylenes in addition to one each of CH, quaternary aromatic carbon and carbonyl carbon. The HETCOR NMR experiment revealed the carbon proton connectivity of the molecule. COSY90 NMR experiment of the compound revealed the coupling between signals at δ 0.88 and 1.26, 0.93 and 1.45, 1.45 and 4.22 and 7.5 and 7.7. Based on these evidence, the structure of the compound was confirmed as 2-methylheptylisonicotinate of formula 1.

d) Biological Activity:

The antibiotic activity of the compound 1 exhibited a wide range of potentialities in both pathogenic fungi and bacteria. The antibacterial activity of it was tested against dominant strains such as *Bacillus subtilis, E. coli, Shigella* sp., *Klebsiella* sp. and *Proteus mirabilis*. Maximum inhibition was recorded in *E. coli* (30 mm in diameter) and *Proteus mirabilis* (28 mm). The remaining strains of *Bacillus subtilis* and *Shigella* sp. showed an inhibition zone of 20 mm each and in *Klebsiella* sp., inhibition zone was 18 mm. The antibiotic compound exhibited promising antifungal activity when tested against dominant fungal pathogens such as *Fusarium moniliformae, F. semitechtum, F. solani, F. oxysporum* and *Rhizactonia solani*. Maximum zone of inhibition was recorded in *Fusarium solani* and *F. semitechtum* (26 mm with 10 μg of the substance), and in *F. oxysporum* inhibition zone was 25 mm. Similar inhibition was also observed in *F. moniliformae* and *Rhizoctonia solani* (24 mm and 22 mm) respectively. The above antibiotic activity against dominant pathogens is the clear indication of the potential application of the compound for both agricultural and medical purposes. The compound is the natural analogue of the established drug isoniazid of formula 2 against tuberculosis (Martindale: The Extra-pharmacopeia, ed. J. E. F. Reynolds, 30th edition, The Pharmaceutical Press, London, U.K., 1993, pp. 174). It may be mentioned that nearly 500,000 patients die of Tuberculosis in India every year and 5.3 million new cases of Tuberculosis are reported every year in the world (Kalia A., 1999, A Deadly Bacilli, A report, 1999, The Statesman, Calcutta, 7th Apr., pp7).

The details of the process disclosed in this invention have been described in the following specific examples which are provided to illustrate the invention only and therefore these should not be construed to limit the scope of the present invention:

EXAMPLE 1 a) Isolation of the *Streptomyces* sp. 201:

A loopful of spores from slant cultures of *Streptomyces* sp. 201, grown on nutrient agar was inoculated in Thronton's medium, at 30° C. in a gyratory shaker, 3.3 Hz, at 200 r.p.m. for 6 days. Both live broth and purified compound from the live broth showed very good antibacterial and antifungal activities against a number of pathogenic organisms such as, *Bacillus subtilis, Shigella* sp., *Klebsiella* sp., *E. coli*, and *Proteus mirabilis Fusarium moniliformae, F. semilechtum, F. oxysponim, F solani* and *Rhizoctonia solani*.

The strain was collected from tea garden soils in Jorhat, Assam (26°44N' and 94°10'E). The morphological and physiological observation of *Streptomyces* sp. 201 on nutrient agar exhibited flexible hyphae from branched aerial mycelium. Most of the mature spore chains comprised of comprised of 30 or more spores (0.7~1.0×1.0~1.32 μm) with smooth surface. No sporongia or synnemata were observed.

The vegetative mycelia were not fragmented into Bacillary and coccoid forms and the conidia were borne as sporophores indicating that the organisms belongs to the family *Streptomycetaceae* and to the genus *Streptomyces*, as evident by the production of chains of conidia in aerial hyphae.

b) Isolation of 2-methylheptylisonicotinate of formula I:

Bio-active compound was isolated as an oil by removing the cell mass through centrifugation followed by extraction (ethyl acetate) and purification by TLC. However, cell mass can also be extracted with chloroform, dichloromethane, ethylene dichloride and other halogenated solvents, hexane, heptane, petroleum ether (40–60° C. fraction, 60–80° C. fraction or 80–100° C. fraction), and other petroleum derived solvents, methyl acetate, propyl acetate, benzene, toluene or any organic solvent. The purification can be affected with column chromatography, medium pressure liquid chromatography (MPLC), high pressure liquid chromatography (HPLC) or other chromatographic methods. Purification can also be affected with fractional distillation, short path distillation etc. Compound was analyzed by elemental analysis, EIMS, UV Spectrum, IR Spectrum, 1H NMR spectrum, DEPT, HETCOR and COSY90NMR experiments to confirm the structure of the compound 2-methylheptylisonicotinate 1.

EXAMPLE 2 a) Isolation of *Streptomyces* sp. 201:

Strains were collected from tea garden soil collected within 15 km radius of Jorhat (26°44N' and 94°10'E) in Assam. Screening of the strains were monitored by testing antifungal and antibacterial activity, following agar cup assay method (Gramer, 1976). Maximum activity of the bioactive molecule was observed with 6 days grown culture broth.

Melanin formation was studied in tyrosine agar medium (Waksman, 1961) containing tyrosine and yeast extract. Nitrate reduction was determined by culturing the strains in medium containing $KNO_3$ (0.1 w/v) and nitrate reduction tested positive in this strain, whereas starch hydrolysis, $H_2S$ production and citrate utilisation was negative (Table 2).

A loopful of spores from slant cultures of *Streptomyces* sp. 201, grown on nutrient agar was inoculated into 250 ml Erlenmeyer flask containing 25 ml of Thronton's medium consisting of in g/L: $K_2HPO_4$ 1, $KNO_3$ 0.5, $MgSO_4$ 0.2, $CaCl_2.2H_2O$ 0.1, asparagine 0.5, mannitol 0.1, NaCl 0.1, $FeCl_3$ 0.01 at pH of 7.4. Inoculated culture broth was incubated at 30° C. in a gyratory shaker, 3.3 Hz, at 200 r.p.m. (Clim-O-Shake, Adolf Kuhenen AG) for 6 days.

b) Biological Activity of the Live Broth:

Live broth of cultured organism *Streptomyces* sp. 201 showed good antibacterial and antifungal activities against a number of pathogenic organisms. To assess the antifungal activity of live broth, agar cup assay method was done. 200 μl of live broth was added to each agar cup. Zone of inhibition was found more *R. solani* (13 mm), followed by *F. oxysporum* & *F. moniliforme* (12 mm) *F. solani* (11 mm) and *F. semilechtum* (10 mm). Same procedure was followed for antibacterial assay and found more in *E. coli* (12 mm)

followed by *P. mirabilis* and *Klebsiella* sp. (12 mm), *Shigella* sp. (9 mm) and *B. subtilis* (8 mm). (Table 1).

(c) Isolation 2-methylheptylisonicotinate 1:

Bioactive compound was isolated by removing the cell mass through centrifugation at 4000 g for 10 min. and then the filtrate (500 ml) was extracted twice with equal volume of methyl acetate (1:1). The solvent was evaporated and the extract was dried over $Na_2SO_4$ under vacuum to give an oil (3.8 mg). For further purification, the crude extract was subjected to separation by thin layer chromatography (Silica gel G), using benzene: ethylacetate (4:1) as running solvent. Iodine visible compound was eluted from the silica gel with ethyl acetate, which on evaporation under reduced pressure, gave an oil, 3.2 mg. UV-$\lambda_{max}$ at 220 nm; IR(cm): 2935, 2900, 2850, 2335, 2320, 1715, 1560, 1540, 1510, 1462, 1380, 1290, 1085, 1060. $^1$H NMR (assigned by COSY90): δ 0.88 (t, J=7 Hz, 3H, H-7), 0.93 (d, J=7 Hz, 3H, H-8), 1.25–1.41 (6H, overlapping signals of H-4, H-5 & H-6), 1.42 (m, 2H, H-3), 1.45 (m, 1H, H-2), 4.22 (m, 1H, H-1), 7.5 (dd, J=4&6 Hz, 2H, H-3' & 5'), 7.7 (dd, J=4&6 Hz, 2H, H-2' & 6'). $^{13}$C NMR (assigned by HETCOR& DEPT135): δ 11.83 (q, C-7), 14.39 (q, C-8), 23.35 (t, C-6), 24.17 (t, C-5), 29.32 (t, C-4), 30.77 (t, C-3), 39.16 (d, C-2), 68.52 (t, C-1), 129.17 (d, C-3' & 5'), 131.23 (d, C-2' & 6'), 132.87 (s, C-1') and 168.09 (s, COO). MS m/z at: 235 [M$^+$], 149, 126, 122, 106, 113, 99, 78 and 58. Analysis: $C_{14}H_{21}NO_2$ requires C, 71.46%; H, 8.99%; & N, 5.95%; found C, 71.44%; H, 8.91%; & N, 5.96%.

d) Biological Activity:

2-Methylheptylisonicotinate of formula 1 was bioassayed following agar cup assay method (Grammer, 1976). The antibiotic activity of the compound exhibited a wide range of potentialities in both pathogenic fungi and bacteria. The antibacterial activity of the bioactive molecule was tested against dominant bacterial strains such as *Bacillus subtilis, E. coli, Shigella* sp., *Klebsiella* sp. and *Proteus mirabilis*. Maximum inhibition was recorded in *E. coli* (30 mm in diameter) and *Proteus mirabilis* (28 mm). The remaining strains of *Bacillus subtilis* and *Shigella* sp. showed an inhibition zone of 20 mm each and in *Klebsiella* sp., inhibition zone was 18 mm. The antibiotic compound exhibited promising antifungal activity when tested against dominant fungal pathogen such as *Fusarium moniliforme, F. semitechtum, F solani, F oxysporum* and *Rhizoctonia solani*. Maximum zone of inhibition was recorded in *Fusarium solani* and *F. semitechtum* (26 mm with 10 μg of the substance), and in *F. oxysporum* inhibition zone was 25 mm. Similar inhibition was also observed in *F. moniliformae* and *Rhizoctonia solani* (24 mm and 22 mm) respectively (Tables 2, 3 & 4). The above antibiotic activity against dominant pathogens is the clear indication of the potential application of the compound for both agricultural and medical purposes.

EXAMPLE 3 a) Isolation of the *Streptomyces* sp. 201:

Strains were collected from tea garden soil collected within 15 km radius of Jorhat city (26°44' N and 94° 10' E), Assam. Screening of the strains were monitored by testing antifungal and antibacterial activity, following agar cup assay method (Grammer, 1976). Maximum activity of the bioactive molecule was observed with 6 d grown culture broth.

Melanin formation was studied in tyrosine agar medium (Waksman, 1961), containing tyrosine and yeast extract. Nitrate reduction was determined by culturing the strains in medium containing $KNO_3$ (0.1%, w/v), gelatin liquefaction was tested in a medium containing 12% (w/v) gelatin. Melanin formation, gelatin liquefaction and nitrate reduction was tested positive in this strain, whereas starch hydrolysis, $H_2S$ production and citrate utilization was found negative.

A loopful of spores from slant cultures of *Streptomyces* sp. 201, grown on nutrient agar was inoculated into 250 ml Erlenmeyer flask containing 50 ml of Thronton's medium, consisting of (g/l): $K_2HPO_4$ 1, $KNO_3$ 0.5, $MgSO_4$ 0.2, $CaCl_2.2H_2O$ 0.1 asparagine 0.5, mannitol 0.1, NaCl 0.1, $FeCl_3$ 0.01, pH7.4. Inoculated culture broth was incubated at 30° C. in a gyratory shaker, 3.3 Hz, at 200 r.p.m. (Clim-O-Shake, Adolf Kuhenen, AG), for 6 days.

b) Isolation 2-methylheptyl isonicotinateI:

The bioactive compound was isolated by removing the cell mass through centrifugation at 4000 g for 10 min. and then the filtrate (1000 ml) was extracted twice with equal volume of chloroform (1:1). The solvent was evaporated and the extract was dried over $Na_2SO_4$ under vacuum to give an oil (7.6 mg). For further purification, the crude extract was subjected to separation by thin layer chromatography (Silica gel G), using benzene: ethylacetate (4:1) as running solvent. Iodine visible compound was eluted from the silica gel with ethyl acetate, which on evaporation under reduced pressure, gave an oil, 6.4 mg. The compound was analyzed by elemental analysis, EEMS, UV spectrum, IR spectrum, $^1$H NMR spectrum, DEPT, HETCOR and COSY90 NMR experiment to confirm the structure of the compound as 2-methylheptyl isonicotinate 1.

c) Biological Activity:

2-Methylheptylisonicotinate 1 was bioassayed following agar cup assay method (Grammer, 1976). The antibiotic activity of the compound exhibited a wide range of potentialities in both pathogenic fungi and bacteria. The antibacterial activity of the bioactive molecule was tested against dominant bacterial strains such as *Bacillus subtilis, E. coli, Shigella* sp., *Klebsiella* sp. and *Proteus mirabilis*. Maximum inhibition was recorded in *E. coli* (30 mm in diameter) and *Proteus mirabilis* (28 mm). The remaining strains of *Bacillus subtilis* and *Shigella* sp. showed an inhibition zone of 20 mm each and in *Klebsiella* sp., inhibition zone was 18 mm. The antibiotic compound exhibited promising antifungal activity when tested against dominant fungal pathogen such as *Fusarium moniliforme, F. semitechtum, F. solani, F. oxysporum* and *Rhizocionia solani*. Maximum zone of inhibition was recorded in *Fusarium solani* and *F. semitechtum* (26 mm with 10 μg of the substance), and in *F. oxysporum* inhibition zone was 25 mm. Similar inhibition was also observed in *F. moniliformae* and *Rhizoctonia solani* (24 mm and 22 mm) respectively (Table 2, 3 & 4).

The above antibiotic activity against dominant pathogens is a clear indication of potential application of the compound in both agricultural and medical purposes.

TABLE 2

Antimicrobial activity of the purified compound
Strains Inhibition zone (mm) at 10 y.g

| Antifungal activity | | Antibacterial activity | |
|---|---|---|---|
| Fusarinm moniliformae | 24 | Bacillus subtilis | 20 |
| F, semitechtum | 26 | Shigella sp. | 20 |
| F. oxysporum | 25 | Klebsiella sp. | 18 |
| F. solani | 26 | E. coli | 30 |
| Rhizoctonia solani | 22 | Proteus mirabilis | 28 |

TABLE 3

Antifungal activity of bioactive compound 1, and isoniazid

| | MIC (μg/ml) | |
|---|---|---|
| Organisms | Compound 1 | Isoniazid |
| Rhizoctonia solani | 20 | 250 |
| F. moniliformae | 45 | 200 |
| F. solani | 20 | 300 |
| F. semitectum | 20 | 300 |
| F. oxysponim | 43 | 350 |

TABLE 4

Antibacterial activity of bioactive compound 1:

| | MIC (μg/ml) | |
|---|---|---|
| Organisms | Compound 1 | Isoniazid |
| Bacillus subtilis | 50 | 150 |
| E. coli | 70 | 250 |
| Arthrobacter sp. | 40 | 150 |
| Proteus mirabilis | 40 | 200 |
| Shigella sp. | 60 | 300 |
| Klebsiella sp. | 50 | 250 |

TABLE 5

Antifungal and Antibacterial Activity of Bioactive Compound 1, and Isoniazid.

| | MIC (μg/ml) | | | MIC (μg/ml) |
|---|---|---|---|---|
| Fungi | Compound I | Isoniazid | Bacteria | Compound I |
| R solani | 20 | 250 | B. subtilis | 50 | 150 |
| F. moniliforme | 42 | 200 | E. coli | 70 | 250 |
| F. solani | 20 | 300 | Arthrobacter sp. | 40 | 150 |
| F. semitectum | 20 | 300 | P. mirabitis | 40 | 200 |
| F. oxysponim | 45 | 350 | Shigella sp. | 60 | 300 |
| | | | Klebsiella sp. | 50 | 250 |

We claim:

1. An antifungal and antibacterial compound 2-methylheptylisonicotinate of formula 1 below isolated from natural sources:

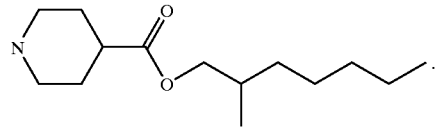

2. A compound as claimed in claim 1 wherein the compound of formula 1 is isolated from *Streptomyces* sp. 201.

* * * * *

UNITED STATES PATENT AND TRADEMARK OFFICE
CERTIFICATE OF CORRECTION

PATENT NO. : 6,998,411 B2
DATED : February 14, 2006
INVENTOR(S) : Gojendra Nath Bordoloi et al.

It is certified that error appears in the above-identified patent and that said Letters Patent is hereby corrected as shown below:

<u>Title page,</u>
Item [75], Inventors, delete "Nabibjyoti Bordoloi, Assam (IN)" and substitute
-- Manobjyoti Bordoloi, Assam (IN) --.
Insert Item -- [30] Foreign Application Priority Data
        India ………..199/DEL/2001-February 27, 2001 --.

Signed and Sealed this

Sixth Day of June, 2006

JON W. DUDAS
*Director of the United States Patent and Trademark Office*